US006594166B2

(12) United States Patent
Chin

(10) Patent No.: US 6,594,166 B2
(45) Date of Patent: Jul. 15, 2003

(54) STEP-UP TRANSFORMER

(75) Inventor: Yem Chin, Burlington, MA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

(21) Appl. No.: 10/103,347

(22) Filed: Mar. 21, 2002

(65) Prior Publication Data

US 2002/0097593 A1 Jul. 25, 2002

Related U.S. Application Data

(62) Division of application No. 09/710,294, filed on Nov. 10, 2000.

(51) Int. Cl.[7] ............................ H02M 5/16; A61B 6/00

(52) U.S. Cl. ........................ 363/171; 336/211; 378/101

(58) Field of Search ............................ 363/171, 75, 80, 363/89, 39, 40, 45; 323/255, 256, 257, 340, 359; 336/129, 134, 136, 211, 220, 234; 378/121, 101, 122

(56) References Cited

U.S. PATENT DOCUMENTS

| | | | | |
|---|---|---|---|---|
| 3,906,333 A | * | 9/1975 | Lalmanash | 323/259 |
| 4,323,736 A | * | 4/1982 | Strickland | 381/116 |
| 4,641,649 A | | 2/1987 | Walinsky et al. | |
| 4,652,846 A | | 3/1987 | Sobottka | |
| 4,858,095 A | * | 8/1989 | Narita et al. | 363/75 |
| 4,860,744 A | | 8/1989 | Johnson et al. | |
| 4,993,404 A | | 2/1991 | Lane | |
| 5,006,119 A | | 4/1991 | Acker et al. | |
| 5,041,107 A | | 8/1991 | Heil, Jr. | |
| 5,084,061 A | | 1/1992 | Gau et al. | |
| 5,127,394 A | | 7/1992 | Lane | |
| 5,151,100 A | | 9/1992 | Abele et al. | |
| 5,230,349 A | | 7/1993 | Langberg | |
| 5,354,220 A | | 10/1994 | Ganguly et al. | |
| 5,372,603 A | | 12/1994 | Acker et al. | |
| 5,392,020 A | * | 2/1995 | Chang | 336/200 |
| 5,542,928 A | | 8/1996 | Evans et al. | |
| 5,562,633 A | | 10/1996 | Wozencroft | |
| 5,566,221 A | | 10/1996 | Smith et al. | |
| 5,591,162 A | | 1/1997 | Fletcher et al. | |
| 5,599,346 A | | 2/1997 | Edwards et al. | |
| 5,704,914 A | | 1/1998 | Stocking et al. | |
| 5,718,688 A | | 2/1998 | Wozendroft | |
| 5,782,740 A | | 7/1998 | Schneiderman | |
| 5,793,272 A | | 8/1998 | Burghartz et al. | |
| 5,795,339 A | | 8/1998 | Erskine | |
| 5,816,999 A | | 10/1998 | Bischoff et al. | |
| 5,865,806 A | | 2/1999 | Howell | |

FOREIGN PATENT DOCUMENTS

| | | |
|---|---|---|
| WO | 97/07740 | 3/1997 |
| WO | 98/48899 | 11/1998 |
| WO | 00/09212 | 2/2000 |

* cited by examiner

*Primary Examiner*—Rajnikant B. Patel
(74) *Attorney, Agent, or Firm*—Fulbright & Jaworski L.L.P.

(57) ABSTRACT

A step up transformer has an inert core, primary windings concentrically surrounding the inert core, and secondary windings concentrically surrounding the primary windings, the ratio of secondary windings to primary windings of up to 1,000,000:1. The step-up transformer is particularly useful in an x-ray catheter having an x-ray source in a vacuum tube and a power source. The power source can deliver a lower voltage which is stepped up at by the transformer to produce a voltage sufficient to stimulate production of x-rays by the x-ray emitter source. Methods for preparing the step-up transformer and x-ray catheter and methods of administering x-rays to subjects with the x-ray catheter of the invention are also disclosed.

15 Claims, 2 Drawing Sheets

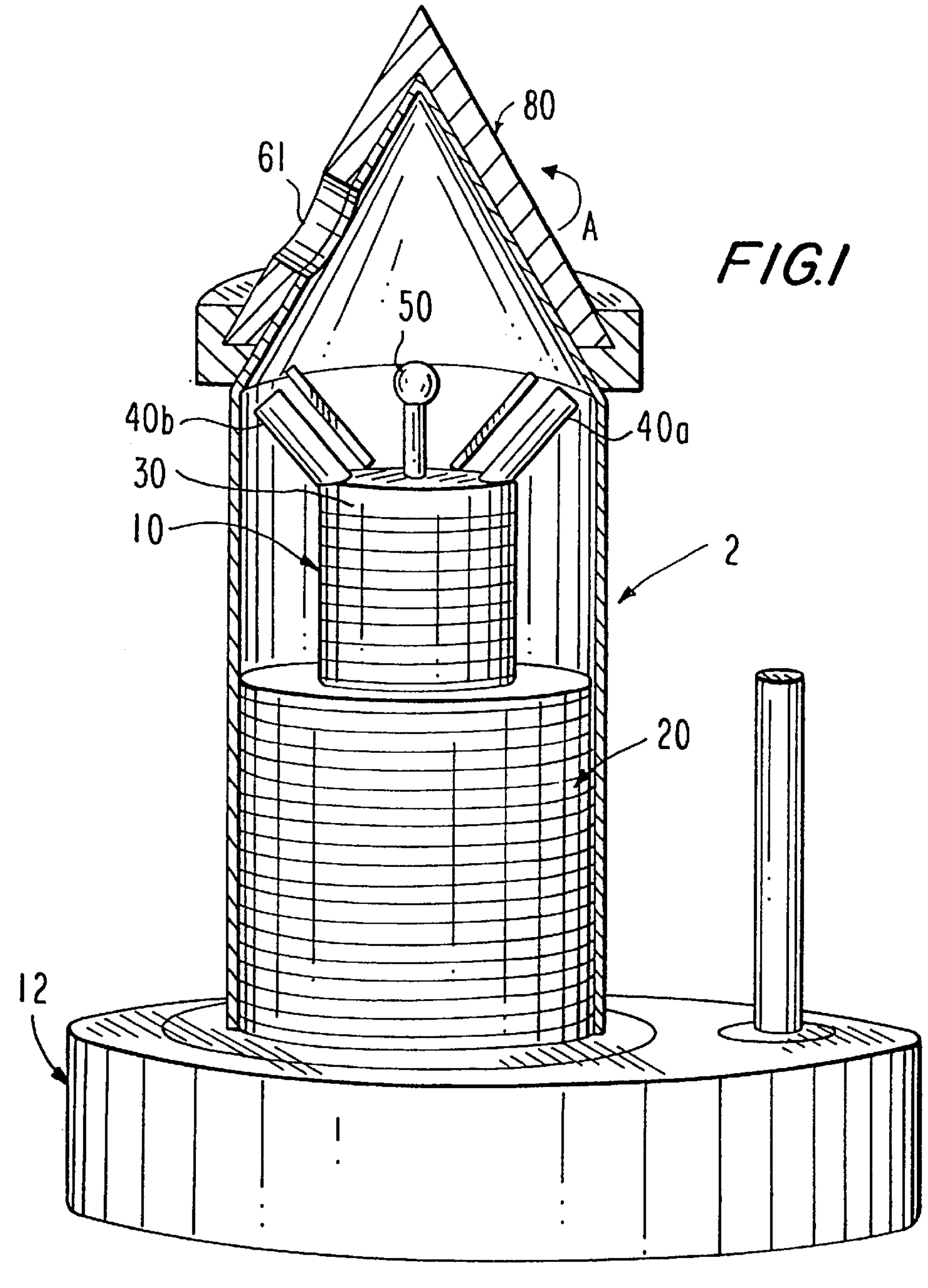
FIG. 1
FIG. 2
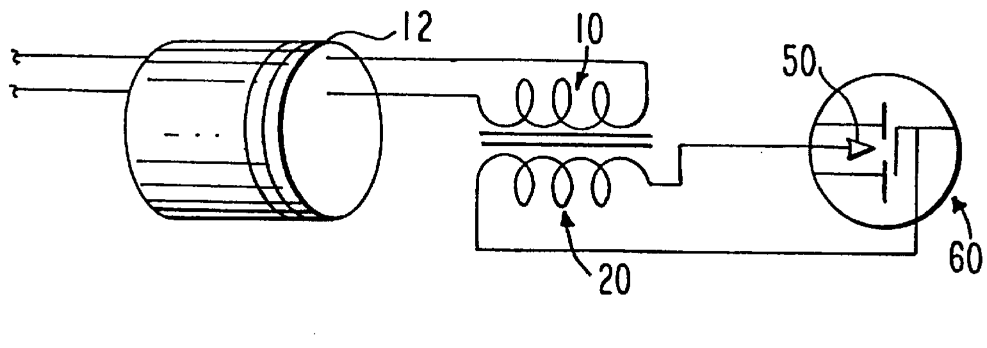

STEP-UP TRANSFORMER

This application is a divisional application of U.S. Ser. No. 09/710,294 filed Nov. 10, 2000.

FIELD OF THE INVENTION

The present invention relates to a step up transformer used to supply energy to a miniaturized x-ray source located in an x-ray catheter by stepping up the voltage at the distal end of the catheter to provide the high voltage, e.g. 10,000–60,000 volts. Such high voltages are needed to accelerate electrons to create x-rays necessary for the intended therapeutic use. The step up transformer allows transmission of a lower voltage down the length of the x-ray catheter than would otherwise be necessary, allowing for safer operation of the x-ray device by minimizing hazards to both operator and patient.

BACKGROUND AND SUMMARY OF THE INVENTION

Traditionally, x-rays have been used in the medical industry to view bone, tissue and teeth. X-rays have also been used to treat cancerous and precancerous conditions by exposing a patient to x-rays using an external x-ray source. Treatment of cancer with x-rays presents many well documented side effects, many of which are due to the broad exposure of the patient to the therapeutic x-rays.

Minimally invasive endoscopic techniques have been developed and are used to treat a variety of conditions. Endoluminal procedures are procedures performed with an endoscope, a tubular device into the lumen of which may be inserted a variety of rigid or flexible tools to treat or diagnose a patient's condition.

The desire for improved minimally invasive medical devices and techniques have led to the development of miniaturized x-ray devices that may be used in the treatment or prevention of a variety of medical conditions. International Publication No. WO 98/48899 discloses a miniature x-ray unit having an anode and cathode separated by a vacuum gap positioned inside a metal housing. The anode includes a base portion and a projecting portion. The x-ray unit is insulated and connected to a coaxial cable which, in turn, is connected to the power source. An x-ray window surrounds the projecting portion of the anode and the cathode so that the x-rays can exit the unit. The x-ray unit is sized for intra-vascular insertion, and may be used, inter alia, in vascular brachytherapy of coronary arteries, particularly after balloon angioplasty.

International Publication No. WO 97/07740 discloses an x-ray catheter having a catheter shaft with an x-ray unit attached to the distal end of the catheter shaft. The x-ray unit comprises an anode and a cathode coupled to an insulator to define a vacuum chamber. The x-ray unit is coupled to a voltage source via a coaxial cable. The x-ray unit can have a diameter of less than 4 mm and a length of less than about 15 mm, and can be used in conjunction with coronary angioplasty to prevent restenosis.

One difficulty encountered in miniaturized x-ray technology is generating the amount of voltage necessary to produce x-ray source while located inside the body. In other applications, transformers have been used to assist generating the required voltages. For example, U.S. Pat. No. 4,652,846 discloses a transformer of small installed volume, which affords, besides electrical separation, an effective static protective shield between the power supply side and the user side, along with simple production and assembly. To accomplish this, a two-chamber transformer with a coil formed for the primary winding and a coil formed for the secondary winding is used. Both are plugged one behind the other onto the transformer core in the direction of the coil axes and a stamped metal foil frame is used as a shielding wall between the adjacent face flanges of the coil forms used. The transformer is particularly well suited for application in equipment of the entertainment, communications and medical technologies.

U.S. Pat. No. 5,793,272 discloses a high quality factor (Q) spiral and toroidal inductor and transformer that are compatible with silicon Very Large Scale Integrations (VLSI) processing, which consume a small IC and operate at high frequencies. The spiral inductor has a spiral metal coil deposited in a trench formed in an dielectric layer over a substrate. The metal coil is enclosed in ferromagnetic liner and capped layers, and is connected to an underpass contact through a metal filled via in the dielectric layer. The spiral inductor also includes ferromagnetic coil lines surrounded by the metal spiral coil. A spiral transformer is formed by vertically stacking the two spiral inductors, while placing them side by side over a ferromagnetic bridge formed below the metal coils and core lines. The toroidal inductor includes a toroidal metal coil with a core having ferromagnetic strips. The toroidal metal coil is segmented into two coils, each having a pair of ports to form a toroidal transformer.

The present invention provides a step up transformer that overcomes difficulties associated with generating sufficient energy to generate x-rays in a miniaturized x-ray source.

SUMMARY OF THE INVENTION

The present invention relates in part to a step-up transformer capable of boosting voltage from a power source to at least 100 times, and preferably at least 1000 times, the voltage of the power input. The transformer includes primary electrically conductive windings surrounding a non-electrically conductive core. Secondary windings surround the primary windings, preferably in a ratio of 1000:1. The transformer is compact, e.g., from 2 to 25 mm and are particularly suited for use with x-ray catheters that generate x-rays at a power source when placed inside the body of a patient.

The present invention also relates to x-ray catheters having the step-up transformer. The x-ray catheter will include an x-ray emitter source, which typically will comprise an anode/cathode arrangement inside a vacuum tube, which is operably connected to a power source. The transformer is operably connected to the power source, and increases the voltage from the power source to a voltage sufficient to generate x-rays at the x-ray emitter source.

Methods of treating patients with the device are also a feature of the invention.

BRIEF DESCRIPTION OF THE DRAWINGS

FIG. 1 is an elevational view of a preferred step up transformer according to the present invention.

FIG. 2 is a circuit diagram of miniaturized x-ray source of the present invention inside an endoscope.

DETAILED DESCRIPTION OF THE INVENTION

Figure 3:
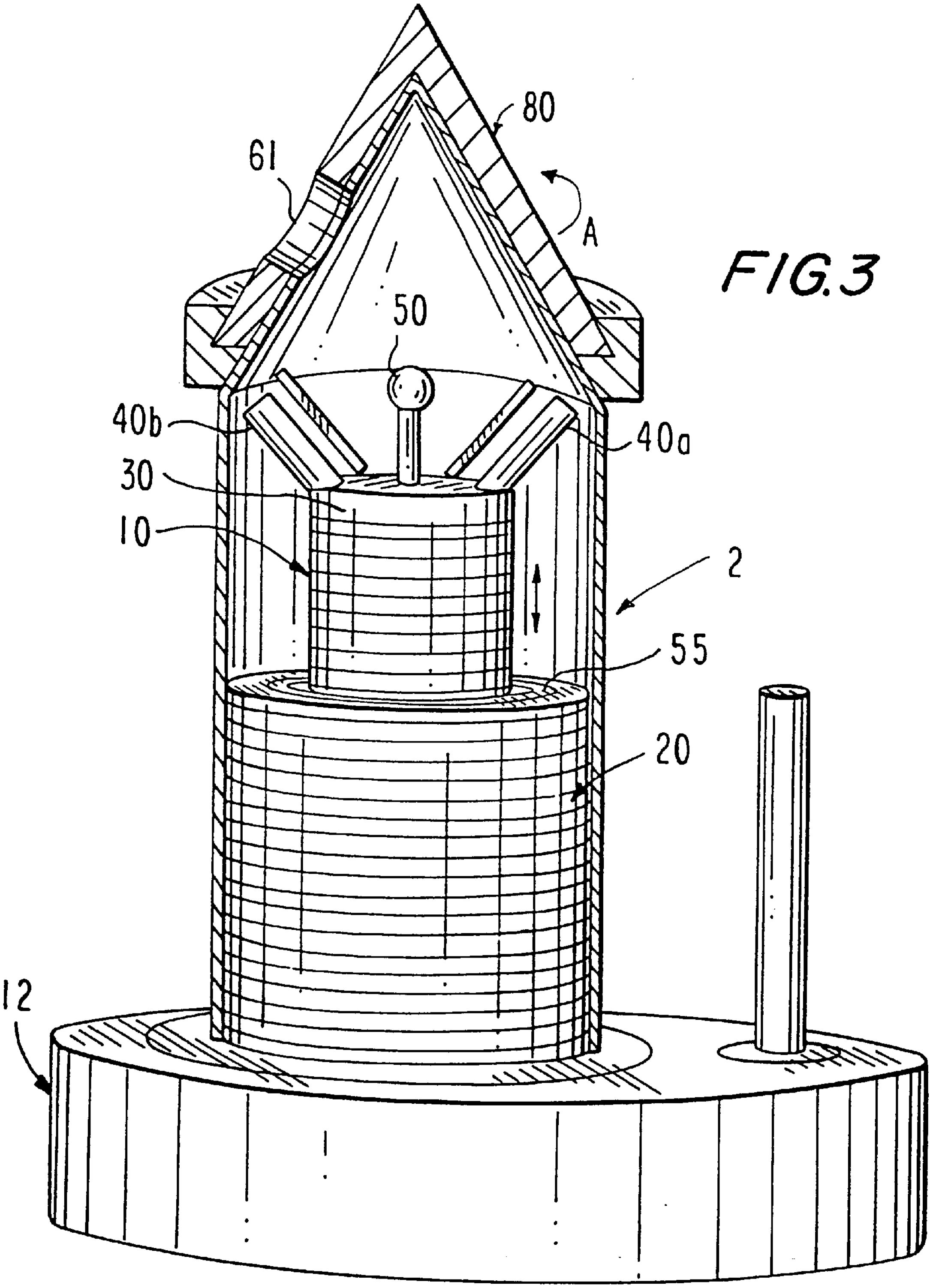
FIG. 3 is an elevational view of a preferred step-up transformer according to the present invention.

Referring to the FIG. 1 step-up transformer 2 includes primary windings 10 concentrically wrapped around non-electrically conductive core 30. Secondary windings 20 contact with and surround primary windings 10. Primary windings 10 and secondary windings 20 are made of an electrically conductive material such as copper. Preferably, the primary windings and secondary windings are 1 mm in diameter or less, e.g. from 1 to about 0.01 mm, to minimize the size of the transformer. Outer sheath 12 is made of an electrically non-conductive material such as a plastic and surrounds the electrically conductive wires (not shown in FIG. 1) which in turn are operatively connected to the power source. The electrically conductive wires are made of copper, aluminum or other conductive metal. Anodes 40*a*, 40*b* are operably connected to primary winding 10 and secondary windings 20 and project distally near emitter 50 but are spaced apart therefrom to provide the necessary potential. Shield 80 is made of an x-ray impenetrable material x-ray absorbing material and is located at the distal end of x-ray catheter 2 and has a window therein so that x-rays may exit the core of the device and irradiate the target tissue. Shutter 61 is retractably affixed to rotator able shield 80 and retractable or rotatable over window 60 to open or close the window to the external environment to allow the passage of x-rays therethrough. X-ray emitter 50 and step-up transformer 2 are positioned in a sealed vacuum tube so as not to be exposed to the external environment. The rotatable shield 80 rotates about axis A as shown in FIG. 1 to properly position shutter 61 to irradiate only the desired tissue, reducing the possibility of damaging healthy tissue.

The ratio of the number of windings between secondary windings 20 and primary windings 10 create the desired increase in voltage. For example, if the secondary windings have 100,000 turns and the primary windings have 100 turns, the ratio of 100,000/100 equates to a 1,000× multiplier step up in voltage. Thus, by transmitting 10 volts of energy down the length of the device, 10,000 volts are created at the secondary windings. A very high ratio, e.g. from of 1,000,000 to 1 of secondary winding to primary windings provides a unique way of providing the voltages necessary to create x-rays at the location of the x-ray emitter, while making for an overall safer and effective apparatus.

Advances in semiconductor wiring allow for the design of the transformers of the present invention at Very Large Scale Integration (VLSI). Disk drive heads and semiconductor wiring are used to create three-dimensional structures using very small geometry wires. Wiring systems that have wires in the order of one micron in length and width are very easily designed using VLSI technology. A step up transformer according to the invention having turn-ratios of 1,000,000 to 1 may be provided within physical constraints in the order of millimeters, e.g. 1 to 10 mm. It is contemplated that the step up transformer of the invention may be used in other applications besides generation of x-rays where high voltages are required but transmission of high voltages to the source is problematic for any variety of reasons.

Transformer wire thickness is essential to create sufficient windings to provide the necessary step up in voltage, and transformers must typically fit within a 25 millimeter length 4 millimeter diameter area. In a preferred embodiment windings are wrapped there around at preferably ferrite core having a one millimeter diameter. Preferably, the wire is on the order of 0.005 mm to 0.05 mm thick and are insulated. Suitable wire can be produced using VLSI techniques or by using packing techniques on a circular wafer. The metal is preferably insulated in a flexible insulator film, such as Kapton. To produce these, metal lines are etched to yield the wire 0.005 mm thick and 0.005 mm wide separated by 0.01 mm. A Kapton film is then overcoated on the surface of the wires completely insulating the wire and a Kapton film is etched between the metal lines. The circular wafer is spun as the wire is wrapped around the core, unwinding the wire from the disk onto the core. The total 0.01 mm diameter will create 25/0.01 windings per winding core length around the core, or 2,500 windings. At 0.01 mm per length thickness, the 2 mm wiring thickness there is provided a 2 mm/0.01 mm or 200 winding layers. At 200 winding layers times 2,500 windings per layer there are provided 500,000 windings. A 500,000 secondary to 50 primary winding ratio results, that is 10,000 to 1. Thus, an input voltage of 3–10 volts in the primary windings will be stepped up to 30,000–100,000 volts output on the secondary windings.

FIG. 2 shows a circuit diagram showing primary wire 10 running through the lumen of catheter 12 and second wire 20 connected to the emitter 50 and plate of the x-ray device.

The windings can be made in a number of different ways. Presently, endoscopic devices manufactured with flexible guide wires are made of a single wire wound in cylindrical fashion. This technology can be used to create windings of less density. These guide wires are made of 0.3 mm diameter wire, which is commercially available.

In another embodiment of the invention shown in FIG. 3, the inner core of the transformer has a sleeve 55 between it and the outer core, allowing the inner core 10 to move within the outer core 20. This arrangement varies the transformer step up, and is used to adjust the output voltage from the secondary windings.

Other embodiments of the invention will become readily apparent to those skilled in the art and are intended hereto to be encompassed by the claims appended hereto.

It is claimed:

1. A step-up transformer comprising:

a non-electrically conductive core;

primary wire windings concentrically wrapped around said non-electrically conductive core; and secondary wire windings concentrically wrapped around said primary wire windings in a ratio of 1000:1.

2. The transformer of claim 1, further comprising a sleeve between said primary wire windings and said secondary wire windings, via which said primary wire windings may pass through said secondary wire windings.

3. A step-up transformer comprising:

a non-electrically conductive core;

primary wire windings concentrically wrapped around said non-electrically conductive core; and secondary wire windings concentrically wrapped around said primary wire windings in a ratio of from 1000:1 to 1,000,000:1.

4. The transformer of claim 3, further comprising a sleeve between said primary wire windings and said secondary wire windings, via which said primary wire windings may pass through said secondary wire windings.

5. The transformer of claim 1, wherein said secondary wire windings have a diameter of one micron.

6. The transformer of claim 3, wherein said secondary wire windings have a diameter of one micron.

7. The transformer of claim 1, wherein at least one of said primary wire windings and said secondary wire windings are copper.

8. The transformer of claim 2, wherein at least one of said primary wire windings and said secondary wire windings are copper.

9. The transformer of claim 3, wherein at least one of said primary wire windings and said secondary wire windings are copper.

10. The transformer of claim 4, wherein at least one of said primary wire windings and said secondary wire windings are copper.

11. The transformer of claim 1, wherein the diameters of each of the primary wire windings and secondary wire windings range from 0.005 mm to 0.05 mm.

12. The transformer of claim 1, wherein the diameters of each of the primary wire windings and secondary wire windings range from 0.005 mm to 0.05 mm.

13. The transformer of claim 3, wherein the diameters of each of the primary wire windings and secondary wire windings range from 0.005 mm to 0.05 mm.

14. The transformer of claim 1, wherein at least one of the primary wire windings and secondary wire windings are insulated.

15. The transformer of claim 3, wherein at least one of the primary wire windings and secondary wire windings are insulated.

* * * * *